(12) United States Patent
Bavouzet et al.

(10) Patent No.: US 7,579,400 B2
(45) Date of Patent: *Aug. 25, 2009

(54) PARTICLES HAVING AN ORGANIZED INTERNAL STRUCTURE WHICH ARE DISPERSED IN AN AQUEOUS PHASE, THE PREPARATION THEREOF AND USE OF SAME

(75) Inventors: Bruno Bavouzet, Gentilly (FR); Jochen Beyermann, Basel (DE); Pascal Herve, Lyons (FR)

(73) Assignee: Rhodia Chimie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/497,882

(22) PCT Filed: Dec. 10, 2002

(86) PCT No.: PCT/FR02/04275

§ 371 (c)(1),
(2), (4) Date: Jun. 23, 2005

(87) PCT Pub. No.: WO03/050166

PCT Pub. Date: Jun. 19, 2003

(65) Prior Publication Data

US 2005/0245672 A1    Nov. 3, 2005

(51) Int. Cl.
*C08L 39/00* (2006.01)
*C08L 33/00* (2006.01)
*C08G 81/02* (2006.01)
*C08K 3/00* (2006.01)

(52) U.S. Cl. .................. 524/516; 524/80; 524/514; 524/556

(58) Field of Classification Search ................. 524/556, 524/514, 80, 516
See application file for complete search history.

(56) References Cited

U.S. PATENT DOCUMENTS

| 5,720,964 | A  | * | 2/1998  | Murray ..................... 424/401 |
| 6,008,184 | A  | * | 12/1999 | Pluyter et al. ............... 510/524 |
| 6,663,855 | B2 | * | 12/2003 | Frechet et al. ........... 424/70.11 |
| 6,933,340 | B2 | * | 8/2005  | Herve et al. ................ 524/522 |
| 7,056,532 | B1 | * | 6/2006  | Kabanov et al. ............ 424/486 |
| 7,176,170 | B2 | * | 2/2007  | Dubief et al. ............... 510/122 |

* cited by examiner

Primary Examiner—Vasu Jagannathan
Assistant Examiner—Karuna P Reddy
(74) Attorney, Agent, or Firm—Hunton & Williams LLP

(57) ABSTRACT

The invention relates to particles comprising: at least one ionically-charged water-soluble polymer; at least one surfactant having an ionic charge opposite to that of said polymer; and at least one water-soluble block copolymer having at least one non-ionic hydrophilic block and at least one non-ionic hydrophobic or ionic block. The invention also relates to a method of obtaining such particles consisting in: preparing a first aqueous mixture comprising the water-soluble, ionically-charged polymer and, if necessary, the water-soluble block copolymer if said copolymer has the same charge; subsequently, a second mixture is added to the above mixture, said second mixture comprising the surfactant and, if necessary, the water-soluble block copolymer if said copolymer has the same charge as the surfactant or if it is not ionically charged. Furthermore, the invention relates to the use of water-soluble block copolymers as an agent for stabilizing particles with a mesophase-forming internal structure, the internal structure of the resulting particles forming the same mesophase.

23 Claims, No Drawings

PARTICLES HAVING AN ORGANIZED INTERNAL STRUCTURE WHICH ARE DISPERSED IN AN AQUEOUS PHASE, THE PREPARATION THEREOF AND USE OF SAME

This application is an application under 35 U.S.C. Section 371 of International Application Number PCT/FR02/04275 filed on Dec. 10, 2002.

The present invention relates to particles in suspension in an aqueous phase, whose internal phase is organized as a mesophase, which comprise an ionically charged water-soluble polymer, a surfactant having a charge opposite to that of the aforementioned polymer, and a water-soluble block copolymer.

Aqueous mixtures comprising a polymer and a surfactant having opposite ionic charges generally lead to the macroscopic separation of the phases, one of which is concentrated with surfactant and polymer, the other diluted.

The concentrated phase may under certain conditions be a structured phase and may exhibit a lamellar, cubic or hexagonal order, etc.

Recently it has been possible, starting from an organized phase of this kind, to obtain, via a process involving a solvent, an aqueous redispersion of particles nanometric in size, comprising an organized phase of surfactant and of polymer.

However, this type of process presents a number of drawbacks. To start with the process is complex and requires the use of an organic solvent. Moreover, the concentration of particles in suspension that can be attained by employing such processes remains too low.

One of the objectives of the present invention is to provide particles with an organized internal structure which comprise a charged polymer and a surfactant having an opposite charge, which are stable in aqueous solution and whose concentration is higher than those attained by conventional processes.

Another objective of the present invention resides in the development of a simple process which does not employ compounds that might give rise to problems of toxicity or ecotoxicity.

These aims and others are achieved by the present invention, which accordingly first provides particles based on at least one ionically charged water-soluble polymer, at least one surfactant having an ionic charge opposite to that of said polymer, at least one water-soluble block copolymer possessing at least one nonionic hydrophilic block A and at least one nonionic hydrophobic or ionic block B, the particles optionally comprising at least one active substance; the internal structure of the particles forming a mesophase; and the particles being in suspension in an aqueous phase.

The invention further provides a process for preparing the particles, in which the following steps are implemented:
a first aqueous mixture is prepared, comprising the ionically charged water-soluble polymer and where appropriate the water-soluble block copolymer if its charge is the same;
a second aqueous mixture is prepared, comprising the surfactant and where appropriate the water-soluble block copolymer if its charge is the same as the surfactant or if it has no ionic charge;
the second mixture is added to the first.

The invention additionally relates to the use of said particles as a surface-state modifier, as an active substance carrier, in formulations intended for treating the hair and/or skin, intended for treating textiles, intended for treating and/or forming metals, or else applicable in the plant health field.

The invention further provides formulations intended for applications in the abovementioned fields and comprising the aforementioned particles.

Finally the invention lastly provides for the use of water-soluble block copolymers possessing at least one nonionic hydrophilic block A and at least one nonionic hydrophobic or ionic block B as a stabilizer of particles whose internal structure forms a mesophase and which comprise at least one ionically charged water-soluble polymer and at least one surfactant having an ionic charge opposite to that of the polymer; the internal structure of the resultant particles, which are in suspension in an aqueous phase and comprise the ionically charged polymer, the surfactant and the block copolymer, forming the same mesophase.

The particles according to the invention can be obtained by implementing a simple process and their concentration in suspension is higher than that attained by conventional processes.

Moreover the particles according to the invention have the advantage of being stable when dispersed in aqueous medium and, under appropriate conditions, in aqueous medium comprising surfactants.

It has further been observed that the particles according to the invention may comprise one or more active substances. Accordingly the particles according to the invention may be employed as means of encapsulating and carrying active substances.

They may also be used as surface modifiers.

Other advantages and features of the present invention, however, will emerge more clearly when the following description and examples are read.

The particles according to the present invention, in accordance with a first feature, are based on at least one ionically charged water-soluble polymer, at least one surfactant having an ionic charge opposite to that of said polymer, at least one water-soluble block copolymer possessing at least one nonionic hydrophilic block A and at least one nonionic hydrophobic or ionic block B, and optionally at least one active substance.

To start with the ionically charged water-soluble polymer possesses positive charges or negative charges.

Water-soluble polymers are those which, in solution in water at a concentration of between 0.01 and 1%, at a temperature of approximately 20° C., do not give rise, over all or part of the indicated concentration range, to macroscopic phase separation.

Moreover the ionically charged polymer is advantageously a linear polymer.

It is noted that said polymer may further be a homopolymer or a random copolymer.

Where the polymer is a copolymer it is obtained from monomers carrying the same type of ionic charge.

In accordance with one particular embodiment of the invention the monomers from which the charged polymer is obtained are selected such that at least 70 mol % of these monomers are ionically charged under the pH conditions of the composition and of the suspension.

Suitable anionic monomers that may be mentioned include monomers containing at least one carboxylic, sulfonic, sulfuric, phosphonic, phosphoric or sulfosuccinic function, or the corresponding salts.

More particularly the monomers may be elected from:
linear, branched, cyclic or aromatic monocarboxylic or polycarboxylic acids containing at least one ethylenic unsaturation, preferably 2 to 10 carbon atoms and optionally at least one hydroxyl group, the N-substituted derivatives of such acids; monoesters of polycarboxylic acids containing at least one ethylenic unsaturation, preferably 2 to 10 carbon atoms and optionally at least one hydroxyl group;

linear, branched, cyclic or aromatic vinylcarboxylic acids containing 2 to 10 carbon atoms;

amino acids containing one or more ethylenic unsaturations;

alone or in mixtures, their precursors, their sulfonic or phosphonic derivatives, and macromonomers deriving from such monomers, it being possible for the monomers or macromonomers to be in the form of salts.

It is recalled that the term "macromonomer" denotes a macromolecule which carries one or more functions that can be polymerized by the appropriate method (for example, by polycondensation, by polyaddition, by free-radical means).

Examples of anionic monomers that may be mentioned include, without intended limitation:

acrylic acid, methacrylic acid, fumaric acid, itaconic acid, citraconic acid, maleic acid, acrylamidoglycolic acid, 2-propene-1-sulfonic acid, methallylsulfonic acid, styrenesulfonic acid, α-acrylamidomethylpropanesulfonic acid, 2-sulfoethylene methacylate, sulfopropylacrylic acid, bis-sulfopropylacrylic acid, bis-sulfopropylmethacrylic acid, sulfatoethylmethacrylic acid, the phosphate monoester of hydroxyethylmethacrylic acid, and alkali metal salts, such as sodium, potassium or ammonium salts;

vinylsulfonic acid, vinylbenzenesulfonic acid, vinylphosphonic acid, vinylidenephosphoric acid, vinylbenzoic acid, and alkali metal salts, such as sodium, potassium or ammonium salts;

N-methacryloylalanine, N-acryloylhydroxyglycine;

alone or in mixtures, and macromonomers deriving from such monomers.

It would not be outside the scope of the present invention to employ precursor monomers to those which have just been mentioned. In other words these monomers have units which, when incorporated into the polymer chain, may be converted, in particular by a chemical treatment such as hydrolysis, to restore the aforementioned anionic species. For example, the completely or partly esterified monomers of the aforementioned monomers may be employed in order subsequently to be fully or partly hydrolyzed.

As cationic hydrophilic monomers from which the ionically charged polymers may be obtained mention may be made in particular of the following:

aminoalkyl(meth)acrylates and aminoalkyl(meth)acrylamides;

monomers containing at least one secondary, tertiary or quaternary amine function, or a heterocyclic group containing a nitrogen atom, aromatic or nonaromatic, vinylamine and ethyleneimine;

diallyldialkylammonium salts;

alone or in mixtures, or the corresponding salts, and macromonomers deriving from such monomers.

It is recalled that the term "macromonomer" denotes a macromolecule which carries one or more functions that are polymerizable by the selected method of polymerization.

As more specific examples of cationic monomers from which the polymer used according to the invention may be synthesized mention may be made in particular of the following:

dimethylaminoethyl(meth)acrylate, dimethylaminopropyl (meth)acrylate di-tert-butylaminoethyl(meth)acrylate, dimethylaminomethyl(meth)acrylamide, dimethylaminopropyl(meth)acrylamide, trimethylammonioethyl (meth)acrylate chloride, trimethylammonioethyl acrylate methyl sulfate, benzyldimethylammonioethyl (meth)acrylate chloride, 4-benzoylbenzyldimethylammonioethyl acrylate chloride and trimethylammonioethyl-(meth)acrylamido chloride;

ethyleneimine, vinylamine, pyridine, 2-vinylpyridine, 4-vinylpyridine, pyrrolidine, 1-vinyl-2-pyrrolidine, imidazoline, 1-vinyl-3-imidazoline, vinylamine and ethyleneimine;

vinylbenzyltrimethylammonium chloride;

diallyldimethylammonium chloride;

alone or in mixtures, or their corresponding salts, and macromonomers deriving from such monomers.

When the monomers are in the form of salts, and more particularly with quaternized amine functions, of ammonium type $NR_4^+$ with R, identical or different at each occurrence, representing a hydrogen atom, an alkyl or hydroxyalkyl radical containing 1 to 10, preferably 1 to 4, carbon atoms which optionally carries a hydroxyl radical; the counterion may be selected from halides such as, for example, chlorine, sulfates, hydrosulfates, alkyl sulfates (for example containing 1 to 6 carbon atoms), phosphates, citrates, formates and acetates.

The ionically charged water-soluble polymer may optionally comprise monomers which do not carry an ionic charge under the pH conditions of the composition and of the suspension, although this version is not preferred.

If they are present, these monomers are more particularly selected from nonionic hydrophilic monomers or nonionic hydrophobic monomers.

In such a case the latter monomers are present in an amount such that the anionically charged polymer is water-soluble in the sense indicated above.

More particularly, if they are present, the molar percentage of monomers of this type in the polymer is less than or equal to 30%, preferably less than or equal to 10%.

A list of nonionic hydrophilic and hydrophobic monomers will be given subsequently.

The ionically charged polymer may be obtained by employing any type of conventional polymerization, such as anionic polymerization, cationic polymerization, or so-called living or controlled free-radical polymerization. It is likewise possible, depending on the monomers employed, to carry out a group-transfer polymerization or else a ring-opening polymerization, a polyaddition, a polycondensation, or else a polymerization involving transesterification of end groups.

The molar mass of the ionically charged polymers is preferably between 600 and $6 \times 10^6$ g/mol, more particularly between 2000 and 100 000 g/mol, preferably between 2000 and 10 000 g/mol. It is pointed out that the molar masses by weight are absolute masses and are determined by size exclusion chromatography coupled with the MALLS (Multi-Angle Laser Light Scattering) method.

The surfactant forming part of the composition of the particles according to the invention is selected from the species having an ionic charge which is opposite to that of the polymer that has just been described.

Accordingly, when the polymer is anionic, the surfactant is cationic, and vice versa, under the pH conditions of the composition and of the suspension.

Among cationic surfactants mention may be made in particular of primary, secondary or tertiary monoamines or polyamines, or those possessing one or more quaternary ammonium groups, containing more particularly 6 to 40 carbon atoms, said amines being linear or branched aliphatic or aromatic amines, and those optionally containing one or more alkoxylated (ethoxylated and/or propoxylated) groups.

Mention may be made more particularly of hexylamine, octylamine, dodecylamine, stearylamine, hexadecylamine, oleylamine, diaminohexane, diaminoheptane, diaminododecane, benzoctamine, alkyldialkylammonium or alkyltrialkylammonium or alkylbenzyldialkylammonium halides, such as dodecyltrimethylammonium chloride or bromide, hexadecyltrimethylammonium chloride or bromide and benzalkonium chloride or bromide;

piperidinium salts;
imidazoles;
heterocyclic amines;

alone or in a mixture.

Examples of suitable anionic surfactants include the following, alone or in combination:

alkyl ester sulfonates, for example of formula R—CH(SO$_3$M)-COOR', where R represents a $C_8$-$C_{30}$, preferably $C_{14}$-$C_{20}$, alkyl radical, R' a $C_1$-$C_6$, preferably $C_1$-$C_3$ alkyl radical and M an alkali metal cation (sodium, potassium, lithium), a substituted or unsubstituted ammonium cation (methyl-, dimethyl-, trimethyl-, tetramethylammonium, dimethylpiperidinium, etc.) or a cation derived from an alkanolamine (monoethanolamine, diethanolamine, triethanolamine, etc.). Mention may be made in particular of methyl ester sulfonates whose radical R is $C_{14}$-$C_{16}$; alkylbenzenesulfonates, more particularly $C_{14}$-$C_{20}$, primary or secondary alkylsulfonates, especially $C_{14}$-$C_{22}$, alkylglycerol sulfonates, sulfonated polycarboxylic acids, such as those described in GB 1082179, and paraffinsulfonates;

alkyl sulfonates for example of formula ROSO$_3$M, where R represents a $C_{10}$-$C_{24}$, preferably $C_{14}$-$C_{20}$, alkyl or hydroxyalkyl radical and M represents a hydrogen atom or a cation with the same definition as above, and their polyalkoxylated(ethoxylated, propoxylated or combinations thereof) derivatives, such as sodium dodecyl sulfate;

alkyl ether sulfates for example of formula RO(CH$_2$CH$_2$O)$_n$SO$_3$M where R represents a $C_{10}$-$C_{24}$, preferably $C_{14}$-$C_{20}$, alkyl or hydroxyalkyl radical, M represents a hydrogen atom or a cation with the same definition as above, and n varies generally from 1 to 4, and also their polyalkoxylated(ethoxylated, propoxylated or combinations thereof) derivatives, such as lauryl ether sulfate with n=2;

alkyl amide sulfates, for example of formula RCONHR'OSO$_3$M where R represents a $C_2$-$C_{22}$, preferably $C_{14}$-$C_{20}$, alkyl radical, R' a $C_2$-$C_3$ alkyl radical, and M a hydrogen atom or a cation whose definition is the same as above, and also their polyalkoxylated(ethoxylated, propoxylated or combinations thereof) derivatives;

salts of saturated or unsaturated fatty acids, such as $C_8$-$C_{24}$ acids, preferably $C_{14}$-$C_{20}$ acids, N-acyl-N-alkyltaurates, alkylisethionates, alkylsuccinamates and alkylsulfosuccinates, monoesters or diesters of sulfosuccinates, N-acylsarcosinates and polyethoxycarboxylates; and alkyl ester and/or alkyl ether and/or alkyl aryl ether phosphates.

The ionic surfactants may optionally be combined with one or more nonionic surfactants, although this version is not preferred.

In such a case the amount of nonionic surfactant is less than or equal to 30% by weight of the ionic surfactant, preferably less than or equal to 10% by weight of the ionic surfactant.

Among possible nonionic surfactants mention may be made of alcohols, acids, preferably $C_6$-$C_{24}$, mono-, di- and triglycerides, sorbitan esters, fatty amines, di- and tri(1-phenylethyl)phenols, alone or in combination, and also their alkoxylated(ethoxylated, or ethoxylated/propoxylated) derivatives.

It is specified, moreover, that the selection of the ionic surfactant is made depending on the appearance of a mesophase when the surfactant is combined with the ionically charged polymer under the same concentration conditions as those of the particles according to the invention (that is, with respective concentrations of tonically charged polymer and surfactant which are identical to those used for preparing the, particles according to the invention, the block copolymer being excluded).

By mesophase is meant the organized phases of charged polymer/oppositely charged surfactant complexes, such as lamellar phases, hexagonal, cubic and bicontinuous (sponge). Preferably the charged polymer/oppositely charged surfactant complex is of lamellar type.

To specify: when the terms "same mesophase" are used in the context of the invention, this signifies in effect that the same mesophase is retained, but also that it may occur in the form of a mesophase of the same type. By way of illustration, a lamellar mesophase and a spherulitic (onion) mesophase will be considered as being, for the purposes of the invention, a same mesophase.

It is easy for the person skilled in the art to establish what combination of charged polymer and of oppositely charged surfactant may give rise to a complex exhibiting an organized internal structure. Specifically it is sufficient for said person to establish the phase diagram of the polymer, surfactant and water system, to observe whether an organized phase appears in the ternary diagram, and, if so, to determine the composition which allows it to be obtained. Said organized phase is generally in equilibrium with a nonorganized, water-rich, dilute phase, and is present in the form of a macroscopic phase, which cannot be used.

One of the essential features of the present invention lies in the presence of at least one water-soluble block copolymer possessing at least one nonionic hydrophilic block A and at least one nonionic hydrophobic or ionic block B.

Specifically—and this represents another subject of the present invention—it was noticed, completely unexpectedly, that the use of block copolymers of this type made it possible to disperse the aforementioned mesophase in the form of a stable dispersion of particles having nanometric or micrometric size.

In other words, the presence of the block copolymer makes it possible to obtain a stable particle suspension, whereas, used alone, the charged polymer/oppositely charged surfactant system would have led to a macroscopic phase separation.

Additionally it was observed that the internal structure of the particles comprising the charged polymer, the surfactant and the block copolymer formed the same mesophase (in the sense mentioned above) as that obtained without the block copolymer.

The block copolymer thus provides another, completely unexpected feature, namely that of conserving the organized phase which existed initially between the charged polymer and the oppositely charged surfactant. This constitutes an additional advantage of the present invention, since the organized phase itself may provide features which are of interest in terms of future applications of the particles (lubrification, encapsulation).

Finally the presence of this block copolymer makes it possible to obtain particles which have a relatively low average size. Advantageously the particles according to the invention present an average size of between 5 nanometers and 50 µm. The average sizes are measured, more specifically, by means of a Horiba particle size analyzer, and correspond to the volume median diameter, ($d_{50}$), which represents the particle diameter equal to 50% of the cumulative distribution.

As indicated earlier on above, the block copolymer is water-soluble. It will be recalled that a polymer is referred to as being water-soluble when it does not give rise to macroscopic phase separation over all or part of a concentration range in water of between 0.01 and 1% by weight at approximately 20° C.

Furthermore, the block copolymer may have a linear (multiblock) structure, a branched (comb or graft) structure or else a star structure.

The linear block copolymers more particularly have a structure which comprises at least two blocks (diblock).

The block copolymers of branched structure (comb or graft) preferentially have an ionically charged or hydrophobic skeleton on which neutral hydrophilic segments are grafted.

As far as the block copolymers of star structure are concerned, a number of possibilities may be envisaged. According to one particular embodiment, if each branch of the star is considered, said branch may comprise either a block copolymer, preferably a diblock copolymer one of whose blocks is a neutral hydrophilic block (A) and the other of which is an ionic or hydrophobic block (B); or a block (A) or (B).

The block copolymers which have just been detailed are compounds which are well known to the person skilled in the art.

Accordingly the copolymers may be prepared by employing anionic, cationic or so-called living or controlled free-radical polymerizations. It is likewise possible, depending on the monomers employed, to carry out a group-transfer polymerization or else a ring-opening polymerization(particularly an anionic or cationic polymerization) or else a polymerization involving transesterification of end groups.

The polymers are preferably obtained by employing at least one step of living free-radical polymerization.

By way of example of polymerization processes referred to as living or controlled, reference may be made in particular to the xanthate-controlled free-radical polymerization according to the teaching of application WO 98/58914, the dithioester-controlled free-radical polymerization according to the teaching of application WO 97/01478, the nitroxide precursor-mediated polymerization according to the teaching of application WO 99/03894, the dithiocarbamate-controlled free-radical polymerization according to the teaching of application WO 99/31144, and the atom transfer radical polymerization (ATRP) according to the teaching of application WO 96/30421.

The graft or comb polymers may be obtained by methods referred to as direct grafting and copolymerization.

Direct grafting consists in polymerizing the selected monomer(s) by free-radical means in the presence of the polymer selected to form the skeleton of the end product. If the monomer/skeleton pairing and the operating conditions are selected judiciously, then there may be a transfer reaction between the growing macroradical and the skeleton. This reaction generates a radical on the skeleton and the graft grows from this radical. The primary radical obtained from the initiator may also contribute to the transfer reactions.

As far as the copolymerization is concerned, it employs, in a first stage, grafting at the end of the future pendant segment of a polymerizable function by free-radical means. This grafting may be carried out by customary methods of organic chemistry. Then, in a second stage, the macromonomer thus obtained is polymerized with the monomer selected to form the skeleton, and a "comb" polymer is obtained.

In the case of star-type polymers, the syntheses may be classified essentially in two groups. The first corresponds to the formation of the arms of the polymers from a polyfunctional compound which constitutes the center ("core-first" technique) (Kennedy, J. P. et al. *Macromolecules*, 29, 8631 (1996), Deffieux, A. et al. *Ibid*, 25, 6744, (1992), Gnanou, Y. et al. *Ibid*, 31, 6748 (1998)) and the second corresponds to a method in which the polymer molecules which are to form the arms are first synthesized and then joined together on a core in order to form a star-shaped polymer ("arm-first" technique). Among the methods which can be used to join the arms mention may be made in particular of the method which comprises reacting these arms with a compound having a plurality of functional groups that are capable of reacting with terminal antagonistic functional groups of said arms (Fetters, L. J. et al., *Macromolecules*, 19, 215 (1986), Hadjichristidis, N. et al., *Macromolecules*, 26, 2479 (1993), Roovers, J. et al., *Macromolecules*, 26, 4324 (1993)). Mention may also be made of the method that comprises adding a compound having a plurality of polymerizable groups, followed by the polymerization of said arms (Rempp, P. et al., *Polym. Sci. Part C*, 22, 145 (1968), Fetters, L. J. et al., *Macromolecules*, 8, 90 (1975), Higashimura et al., Ibid, 24, 2309 (1991)).

In order to obtain the polymer chains which subsequently form the arms of the stars the general approach is to employ methods which allow the polymerization reaction to be controlled. Accordingly, living anionic and cationic polymerizations are the methods most commonly used at present.

Preferably the block copolymer employed according to the invention are linear copolymers comprising two blocks.

As far as block A is concerned it is obtained from nonionic hydrophilic monomers selected more particularly from ethylene oxide; amides of monocarboxylic or polycarboxylic acids, linear, branched, cyclic or aromatic, containing at least one ethylenic unsaturation or derivatives thereof, such as (meth)acrylamide and N-methylol(meth)acrylamide; hydrophilic esters deriving from (meth)acrylic acid such as, for example 2-hydroxyethyl(meth)acrylate; vinyl esters which make-it possible for polyvinyl alcohol blocks to be obtained after hydrolysis, such as vinyl acetate, vinyl Versatate® and vinyl propionate; and monomers of the sugars type such as glycosides and highly depolymerized polysaccharides.

By highly depolymerized are meant compounds whose weight-average molecule mass is more particularly less-than 20 000 g/mol (determined by size exclusion chromatography coupled with the MALLS (Multi-Angle Laser Light Scattering) method.

Glycosides are compounds resulting from the condensation, with elimination of water, of monosaccharide molecules with one another or else with noncarbohydrate molecules. Among glycosides preference is given to saccharides which are formed by the joining of exclusively carbohydrate units and more particularly oligosaccharides (or oligoholosides), which contain only a limited number of these units, i.e. a number generally less than or equal to 10. Examples of oligosaccharides that may be mentioned include sucrose, lactose, cellobiose and maltose.

Suitable highly depolymerized polysaccharides (or polyholosides) are-described for example in the work by P. Arnaud entitled "cours de chimie organique", published by Gauthier-Villars, 1987. As a nonlimiting example of highly depolymerized polysaccharides mention may be made of dextran or starch.

It should be noted that the abovementioned monomers may also-be employed in the form of macromonomers.

As regards block B, one of the possibilities of the present invention is that this block is obtained from nonionic hydrophobic monomers.

Suitable monomers include:
esters of monocarboxylic or polycarboxylic acids, linear, branched, cyclic or aromatic, containing at least one ethylenic unsaturation;
α,β-ethylenically unsaturated nitriles, vinyl ethers, vinyl esters, vinylaromatic monomers and vinyl or vinylidene halides;
aromatic or nonaromatic, linear or branched hydrocarbon monomers containing at least one ethylenic unsaturation;

alone or in mixtures, and also the macromonomers deriving from such monomers.

As particular examples of monomers which can be used in the preparation of the hydrophobic block or blocks of the block copolymers mention may be made of:
esters of (meth)acrylic acid with an alcohol containing 1 to 12 carbon atoms, such as methyl(meth)acrylate, ethyl (meth)acrylate, propyl(meth)acrylate, n-butyl(meth) acrylate, t-butyl(meth)acrylate, isobutyl(meth)acrylate or 2-ethylhexyl acrylate;
vinyl acetate, vinyl Versatate®, vinyl propionate, vinyl chloride, vinylidene chloride, methyl vinyl ether and ethyl vinyl ether;
vinyl nitrites include more particularly those having 3 to 12 carbon atoms, such as acrylonitrile and methacrylonitrile in particular;
styrene, α-methylstyrene, vinyltoluene, butadiene and chloroprene;

alone or in mixtures, and also macromonomers deriving from such monomers.

Preferred monomers are the esters of acrylic acid with linear or branched $C_1$-$C_4$ alcohols, such as methyl, ethyl, propyl and butyl(meth)acrylates, and vinyl esters such as vinyl acetate, styrene and α-methylstyrene.

According to another possibility of the invention the block B of the block copolymer is obtained from ionic monomers.

A first category of ionic monomers is constituted by cationic monomers.

As examples of monomers of this type mention may be made in particular of:
aminoalkyl(meth)acrylates and aminoalkyl(meth)acrylamides;
monomers containing at least one secondary, tertiary or quaternary amine function, or a heterocyclic group containing a nitrogen atom, vinylamine and ethyleneimine;
diallyldialkylammonium salts;

alone or in mixtures, the corresponding salts, and also macromonomers deriving from such monomers.

A second category of ionic monomers is constituted by anionic monomers.

More particularly it will be possible to use anionic monomers containing at least one carboxylic, sulfonic, sulfuric, phosphonic, phosphoric or sulfosuccinic function, the corresponding salts, and also macromonomers deriving from such monomers.

Advantageously the anionic monomers ate selected from:
linear, branched, cyclic or aromatic monocarboxylic or polycarboxylic acids containing at least one ethylenic unsaturation, preferably 2 to 10 carbon atoms and optionally at least one hydroxyl group, the N-substituted derivatives of such acids; the monoesters of polycarboxylic acids containing at least one ethylenic unsaturation, preferably 2 to 10 carbon atoms and optionally at least one hydroxyl group;
linear, branched, cyclic or aromatic vinylcarboxylic acids containing 2 to 10 carbon atoms;
amino acids containing one or more ethylenic unsaturations;

alone or in mixtures, their precursors, their sulfonic or phosphonic derivatives, and macromonomers deriving from such monomers; the monomers or macromonomers may be in the form of salts.

A more exhaustive description of the anionic and cationic monomers has been given in the section relating to the ionically charged polymer, and reference may be made to that description.

The composition of the A and B blocks of the block copolymers may vary within a wide range provided that said copolymer is water-soluble in the sense of the invention.

It should additionally be noted that according to one particular embodiment of the invention the block copolymer has a weight-average molar mass of between 600 and $10^6$ g/mol, preferably between 2000 and 100 000 g/mol. The weight-average molar masses are absolute masses determined by size exclusion chromatography coupled with the MALLS method.

Furthermore, the mass and the number of neutral hydrophilic blocks are adapted such that the block copolymer is water-soluble and also ensures the dispersion of the particles in the aqueous phase. Advantageously, therefore, the ratio of the molar masses of the blocks A and the blocks B (blocks. A/blocks B) is preferably greater than or equal to 2. The molar masses are weight-average molar masses which are theoretical, that is to say, they are expected at the outcome of the polymerization; they are evaluated as a function of the amount of monomers employed in the polymerization reaction.

According to one more particular feature of the present invention the aqueous dispersion of particles contains an amount of ionically charged polymer of between 0.01 and 30% by weight relative to the aqueous phase, more particularly between 0.05 and 10% by weight, preferably between 0.05 and 2% by weight.

The amount of surfactant is more particularly expressed as a function of the ratio Zs, which corresponds to the molar charge concentration of the surfactant divided by the molar charge concentration of the ionically charged polymer.

According to this criterion the amount of surfactant is preferably such that the ratio Zs is between 0.01 and 100, more particularly between 0.1 and 10, preferably between 1 and 5.

As regards the amount of block copolymer forming part of the aqueous dispersion of particles according to the invention, it will be expressed differently depending on whether the copolymer does or does not include one or more ionically charged blocks, and depending on whether the ionic charge is cationic or anionic.

Where the block copolymer has the same charge as the ionically charged polymer, the amount of block copolymer is determined advantageously as a function of the ratio Zb, corresponding to the molar charge concentration of the surfactant divided by the molar charge concentration of the ionically charged polymer and of the block copolymer. According to this criterion the amount of block copolymer is more particularly such that the ratio Zb is between 0.5 and 1.5, advantageously between 0.8 and 1.2.

Where the block copolymer has a charge opposite to that of the ionically charged polymer, the amount of block copolymer is determined advantageously as a function of the ratio Z'b, corresponding to the molar charge concentration of the surfactant and of the block copolymer divided by the molar charge concentration of the ionically charged polymer, is between 0.5 and 1.5, more particularly between 0.8 and 1.2.

Finally, where the block copolymer does not possess an ionic charge, the amount of this polymer is more particularly between 10 and 100% by weight relative to the weight of ionically charged polymer and of surfactant. In the context of this possibility the ratio Zs, corresponding to the molar charge concentration of the surfactant divided by the molar charge concentration of the ionically charged polymer, is more between 0.5 and 1.5, more particularly between 0.8 and 1.2.

As indicated earlier on above, the particles according to the invention may comprise at least one active substance.

All substances providing an effect in the subsequent application of the particles may be used, provided they are of low or no miscibility in water. By substances of low or no miscibility are meant those whose solubility in water does not exceed 10% by weight, at approximately 20° C., of the particles according to the invention.

These active substances may be present alternatively in a liquid form, dissolved in a sparingly water-miscible or water-immiscible organic solvent in the sense indicated above, or else in a solid form, at approximately 20° C., of the particles according to the invention.

Furthermore, the active substances preferably have a melting temperature of less than or equal to 100° C., more particularly less than or equal to 80° C.

As a suitable compound mention may be made in particular of organic oils, of animal or plant origin, or mineral oils, and also waxes originating from the same origins, or mixtures thereof.

As organic oils of animal origin mention may be made, among others, of cachalot oil, whale oil, seal oil, sardine oil, herring oil, shark oil, cod liver oil; pork fat and mutton fat (tallows).

As waxes of animal origin mention may be made of beeswax.

As examples of organic oils of plant origin mention may be made, among others, of rapeseed oil, sunflower oil, peanut oil, olive oil, walnut oil, corn oil, soybean oil, linseed oil, hemp oil, grapeseed oil, copra oil, palm oil, cottonseed oil, babassu oil, jojoba oil, sesame oil, castor oil, cacao butter and karite butter.

As waxes of plant origin mention may be made of carnauba wax.

Regarding the mineral oils mention may be made, among others, of petroleum cuts, naphthenic oils and liquid paraffins (vaseline). Paraffinic waxes may also be suitable for preparing the emulsion.

Products obtained from the alcoholysis of the aforementioned oils may also be used.

It would not be outside the scope of the present invention to employ, as active substance, at least one saturated or unsaturated fatty acid, at least one saturated or unsaturated fatty alcohol, at least one fatty acid ester, or mixtures thereof.

More particularly, said acids contain 8 to 40 carbon atoms, more particularly 10 to 40 carbon atoms, preferably 18 to 40 carbon atoms, and may contain one or more, conjugated or nonconjugated, ethylenic unsaturations, and optionally one or more hydroxyl groups. As for the alcohols they may contain one or more hydroxyl groups.

Examples of saturated fatty acids that may be mentioned include palmitic, stearic, isostearic and behenic acids.

Examples of unsaturated fatty acids that may be mentioned include myristoleic, palmitoleic, oleic, erucic, linoleic, linolenic, arachidonic and ricinoleic acids and also mixtures thereof.

As regards the fatty acid esters they may advantageously be obtained from abovementioned fatty acids and alcohol containing in particular 1 to 6 carbon atoms. The esters in question are preferably methyl, ethyl, propyl and isopropyl esters.

As for the alcohols they may contain more particularly 4 to 40 carbon atoms, preferably 10 to 40 carbon atoms, optionally one or more, conjugated or nonconjugated, ethylenic unsaturations, and optionally two or more hydroxyl groups. Polymers containing two or more hydroxyl groups may also be suitable, such as polypropylene glycols, for example.

As an example of alcohols mention may be made for example of those corresponding to the aforementioned acids.

Examples that may be mentioned of active substances in the foodstuff field include mono-, di- and triglycerides, essential oils, flavors and colors.

Examples of active substances which can be used in the cosmetics field include silicone oils belonging for example to the class of the dimethicones; coenzyme Q10; lipophilic vitamins, such as vitamin A and its derivatives, particularly its esters such as the acetate, palmitate and propionate, vitamin B2, pantothenic acid, vitamin D and vitamin E; mono-, di- and triglycerides; bactericides; UV absorbers, such as aminobenzoate derivatives of PABA and PARA type, salicylates, cinnamates, anthranilates, dibenzoylmethanes, camphor derivatives and mixtures thereof.

Aging inhibitors may also be used. Examples that may be mentioned of such inhibitors include in particular retinoids, fat-soluble vitamins, vitamin C derivatives such as the esters, particularly the acetate, propionate and palmitate; ceramides and pseudoceramides, phospholipids, fatty acids, fatty alcohols, cholesterol, sterols and mixtures thereof. As preferred fatty acids and preferred alcohols mention may be made more particularly of those which possess linear or branched alkyl chains containing 12 to 20 carbon atoms. The compound in question may in particular be linoleic acid.

It is likewise possible to employ anticellulite agents, such as isobutylmethylxanthine and theophylline in particular; and also antiacne agents, such as resorcinol, resorcinol acetate, benzoyl peroxide and numerous natural compounds.

Flavors, essential oils and perfumes may also be used as a hydrophobic active substance. Reference may be made to the lists of compounds indicated above.

Antimicrobial agents may be selected from thymol, menthol, triclosan, 4-hexylresorcinol, phenol, eucalyptol, benzoic acid, benzoic peroxide, butyl paraben and mixtures thereof.

As examples of active substances suitable for the realization of the invention within the paints field mention may be made of alkyd resins, epoxy resins and blocked or nonblocked isocyanates.

In the paper field mention may be made by way of example of sizing resins and water repellency resins such as alkylketene dimer (AKD) or alkenylsuccinic anhydride (ASA).

In the agrochemical field the active plant health substances may be selected from the class of the α-cyanophenoxybenzylcarboxylates or the α-cyanohalophenoxycarboxylates, the class of the N-methylcarbonates, including aromatic substituents, and active substances such as aldrin, azinphos-methyl, benfluralin, bifenthrin, chlorphoxim, chlorpyrifos, fluchloralin, fluroxypyr, dichlorvos, malathion, molinate, parathion, permethrin, profenofos, propiconazole, prothiofos, pyrifenox, butachlor, metolachlor, chlorimephos, diazinon, fluazifop-P-butyl, heptopargil, mecarbam, propargite, prosulfocarb, bromophos-ethyl, carbophenothion and cyhalothrin.

In the detergents field mention may be made, as a possible active substance, of silicone antifoams.

It is likewise possible to use active substances such as those which form part of the composition of lubricants for the working or forming of materials. The active substance is commonly an oil, an oil derivative or else a fatty acid ester or a fatty acid salt, such as those mentioned above.

The active substance may also be selected from organic solvents or mixtures of such solvents which are immiscible or sparingly miscible in water, such as in particular those employed for cleaning or pickling, such as aromatic petroleum cuts, terpene compounds such as D- or L-limonenes, and also solvents such as Solvesso®. Also suitable as solvents are aliphatic esters, such as the methyl esters of a mixture of acetic, succinic and glutaric acids (an acid mixture which is a byproduct of the synthesis of nylon), oils such as Vaseline oil, and chlorinated solvents.

If one or more active substances are present they represent more particularly an amount of between 0.01 and 100% by weight relative to the weight of ionically charged polymer, surfactant and block copolymer.

The particle dispersion advantageously comprises a particle concentration of between 0.1 and 50% by weight relative the aqueous phase, preferably between 0.1 and 30% by weight relative the aqueous phase.

The particles according to the invention also have an average size of between 5 nanometers and 50 µm, preferably between 50 nm and 5 µm. The average sizes are measured, more specifically, by means of a Horiba particle size analyzer, and correspond to the volume median diameter ($d_{50}$), which represents the particle diameter equal to 50% of the cumulative distribution.

The invention secondly provides a process for preparing the particles which have just been detailed, which consists in implementing the following steps:
- a first aqueous mixture is prepared, comprising the ionically charged polymer and where appropriate the block copolymer if its charge is the same;
- a second aqueous mixture is prepared, comprising the surfactant and where appropriate the block copolymer if its charge is the same as the surfactant or if it has no ionic charge;
- the second mixture is added to the first.

It should be noted that if one or more active substances are employed there are a number of ways in which it or they can be introduced.

According to a first possibility the active substance or substances are introduced into the second aqueous mixture (comprising the surfactant).

According to a second possibility the active substance or substances are introduced once the addition of the second mixture to the first has been made.

A combination of the these two possibilities may be envisaged.

According to one embodiment of the invention the temperature at which the mixtures ate prepared is greater than or equal to the temperature at which aqueous solutions are obtained. Accordingly the temperature is selected such that the surfactant is soluble in the aqueous mixture.

It should further be noted that, where an active substance is present in the mixture comprising the surfactant, the temperature of the mixture is preferably such that said active substance is in the form of a liquid, so as to optimize its dispersion.

By way of illustration the temperature is greater than the ambient temperature, preferably greater than or equal to 20° C., and more preferably still between 20 and 90° C.

Advantageously the temperature of the two aforementioned aqueous mixtures, and also that at which the two mixtures are brought into contact, is the same or near.

In the case where an active substance is incorporated once the dispersion has been obtained (in other words when the two mixtures are contacted) the temperature of the active substance is preferably such that it is in the form of a liquid. It is further specified that, in order to improve the incorporation and homogeneity of distribution of the active substance, the temperature of the dispersion is near to that of the active substance.

Moreover, the pH at which the two mixtures are contacted corresponds preferably to a value at which the mesophase appears between the charged polymer and the surfactant in the presence of the block copolymer.

Commonly the pH is adjusted, if necessary, before the species are contacted with each other. It is, however, not ruled out for the pH to be adjusted when contacting has taken place.

The pH is adjusted in entirely conventional manner, by adding base (such as alkali metal hydroxides, alkali metal carbonates and bicarbonates) or else acid (such as mineral acids of the type of hydrochloric acid, for example).

The two mixtures are contacted in customary manner, with stirring.

The result at the outcome of the contacting operation comprises particles in suspension in an aqueous phase.

When mixing has been carried out and the active substance has been optionally incorporated, the resulting mixture is cooled if the temperature at which it has been produced is greater than or equal to the ambient temperature. This operation may be carried out by leaving the mixture to cool, without special intervention, or else by actively lowering the temperature of the mixture (chilling for example).

The present invention likewise provides for the use of the particles as a surface state modifier.

It additionally provides for the use of the particles as an active substance carrier.

This is because their particular structure makes it possible to encapsulate active substances and to release them. This release may take place under the action of various trigger factors, such as pH changes and shearing among others.

The particles according to the invention may be employed as a constituent element of formulations intended for treating the skin and/or hair, for treating textiles, for treating and/or shaping metals, and in the plant health field.

This is because the particles, under certain conditions, have the advantage of remaining in the form of stable suspensions when they are introduced into formulations containing non-negligible levels of appropriate surfactants.

The invention further provides formulations comprising the particles according to the invention, which are intended for treating the skin and/or hair, for treating and/or forming metals, for the treatment of plants (plant health), in the paper-making industry, etc.

Specific but nonlimitative examples of the invention will now be presented.

EXAMPLE

1/Comparative Experiment

The preparation of the complex of polyethyleneimine and dodecanoic acid is performed as follows:

The coefficient Zs (acid ionic charge/polymer ionic charge) is 0.5.

200.3 mg of dodecanoic acid are dissolved in 10 ml of ethanol.

Then, slowly and at ambient temperature, 88.0 mg of polyethyleneimine (Aldrich; ref. 40,872-7) are added to the aforementioned mixture, in the form of an aqueous solution with a strength of 5% by weight in water.

The resulting transparent solution is subsequently stirred for 30 minutes and then dried at ambient temperature, in the form of a film which comprises the polyethyleneimine/dodecanoic acid complex.

The particles are obtained as follows:

20 mg of the complex obtained above are dissolved in 15 ml of tetrahydrofuran (THF).

Subsequently 20 ml of water are introduced and the resulting mixture is then left at ambient temperature until the odor of the THF can no longer be detected.

The mixture is weighed to determine the amount of water lost during the evaporation of the THF, and a corresponding amount of water is added.

The solids concentration in the dispersion is 0.1% by weight.

An aqueous dispersion is subsequently recovered which comprises dispersed particles.

The particles obtained are characterized by means of a Cryo-TEM (transmission electron microscopy) analysis.

It is shown that the dispersed particles are spherical, that their average size is approximately 90 nm and that their internal structure is of low-order onion type.

Small-angle X-ray scattering analysis confirms the onion-type structure.

It is not possible to reproduce such a method with concentrations of more than 0.2%.

Furthermore, when the coefficient Zs is close to 1, it is not possible to redisperse the particles obtained.

2/Experiment According to the Invention

Preparation of the Cationic Block Copolymer:

(polydimethylaminoethyl acrylate)$_{11\,000}$-Block (acrylamide)$_{30\,000}$.

First Step:

Synthesis of (poly(trimethyl(2-acryloyloxy)ethyl)-ammonium methyl sulfate)$_{11K}$)

An aqueous solution of trimethyl(2-acryloyloxy)ethyl)ammonium methyl sulfate (or TMAEAMS; in solution at 80% in water) is introduced into a reactor and the solution is heated to 70° C.

Then a mixture of S-ethylpropionyl O-ethyl xanthate (or xanthate), 4,4-azobis-4-cyanovaleric acid (or ACVA; 30 mol % relative to the xanthate) and isopropanol is introduced. The mixture thus obtained is stirred for 12 hours at 70° C.

| Mass of reactants introduced | | | | |
| --- | --- | --- | --- | --- |
| TMAEAMS | Water | Xanthate | ACVA | Isopropanol |
| 6.69 g | 8.92 g | 0.103 g | 0.042 g | 1.75 g |

Second Step:

Synthesis of the copolymer polyTMAEAMS$_{11k}$-PAM$_{30k}$

ACVA (50 mol % relative to the xanthate) in solution in water is added to the preceding mixture.

| Mass of reactants introduced | |
| --- | --- |
| ACVA | Water |
| 0.07 g | 26.28 g |

Acrylamide in solution in water (I) is then added continuously over 3 hours.

After the first hour ACVA (22 mol % relative to the xanthate) in solution in water (II) is also added.

| Mass of reactants introduced | | | |
| --- | --- | --- | --- |
| Acrylamide | Water (I) | ACVA | Water (II) |
| 14.6 g | 41.5 g | 0.03 g | 0.05 g |

After the second hour ACVA (22 mol % relative to the xanthate) in solution in water (II) is also added.

| Mass of reactants introduced | |
| --- | --- |
| ACVA | Water |
| 0.03 g | 0.05 g |

After the 3 hours the mixture is left with stirring at 70° C. for 2 additional hours.

The final solids content of the solution is 20%.

Particles are obtained by implementing the following steps:

A first aqueous mixture is prepared, containing 0.1 g of the copolymer obtained above and 0.1 g of polyethyleneimine (Aldrich; high molar mass; ref. 40,872-7) in 30 ml of water.

The pH of the mixture is between 7 and 8.

A second aqueous mixture is prepared, containing 0.48 g of dodecanoic acid in 30 ml of water at 45° C. The pH of this mixture is approximately 7 to 8.

The coefficient Zs is 1.04 and the coefficient Zb is near to 1.

With stirring, the second mixture is slowly introduced into the first.

The theoretical ratio of opposite charges is 1.

This gives a stable dispersion of the latex type with a solids content of 1.1% by weight.

The particles obtained are characterized by Cryo-TEM analysis.

It is shown that the particles are primarily in ellipsoidal form, with an average size of approximately 310 nm.

Moreover, the internal structure of the particles is lamellar, but not onion-type. An uncurved lamellar stack is observed.

Small-angle X-ray scattering analysis confirms this and shows that the internal structure is ordered, with repeat distances of approximately 4 nm.

The invention claimed is:

1. Particles comprising at least one ionically charged polymer, at least one surfactant having an ionic charge opposite to that of said polymer, at least one block copolymer consisting of one nonionic hydrophilic block A and one ionic block B, the particles optionally comprising at least one active substance, the internal structure of the particles forming a mesophase which is the organized phases of charged polymer/oppositely charged surfactant complexes, and the particles being in suspension in an aqueous phase, wherein the monomers from which the ionic block B are formed, are cationic monomers selected from the group consisting of aminoalkyl (meth)acrylates and aminoalkyl(meth)acrylamides;

monomers containing at least one secondary, tertiary or quaternary amine function, or a heterocyclic group containing a nitrogen atom, vinylamine and ethyleneimine; and diallyldialkylammonium salts.

2. The particles as claimed in claim 1, wherein the ionically charged polymer is a homopolymer.

3. The particles as claimed in claim 1, wherein the ionically charged polymer is a random copolymer.

4. The particles as claimed in claim 3, wherein the ionically charged copolymer is obtained from monomers which carry the same type of ionic charge and of which at least 80 mol % is ionically charged under the pH conditions of the composition and of the suspension.

5. The particles as claimed in claim 1, wherein the ionically charged polymer is obtained from nonionic hydrophilic monomers or nonionic hydrophobic monomers; with a molar percentage of said monomers in the polymer being less than or equal to 30%.

6. The particles as claimed in claim 1, wherein the surfactant is an anionic or a cationic surfactant, optionally comprising one or more nonionic surfactants in a proportion of less than 30 mol % relative to the ionic surfactant.

7. The particles as claimed in claim 1, wherein the ionically charged polymer and the surfactant form a mesophase under the same concentration conditions as those of the particles.

8. The particles as claimed in claim 1, wherein the monomers from which the block A are formed are ethylene oxide; amides of monocarboxylic acids linear, branched, cyclic or aromatic, containing at least one ethylenic unsaturation; amides of polycarboxylic acids, linear, branched, cyclic or aromatic, containing at least one ethylenic unsaturation; hydrophilic esters deriving from (meth)acrylic acid; vinyl esters which allow polyvinyl alcohol blocks to be obtained after hydrolysis; or monomers of the sugars type.

9. The particles as claimed in claim 1, wherein the ratio of the theoretical molar masses by weight is greater than or equal to 2.

10. The particles as claimed in claim 1, wherein the ionically charged polymer is present in an amount of between 0.01 and 30% by weight relative to the aqueous phase.

11. The particles as claimed in claim 10, wherein the ionically charged polymer is present in an amount of between 0.05 and 2% by weight relative to the aqueous phase.

12. The particles as claimed in claim 1, wherein the surfactant is present in an amount such that the ratio Zs, corresponding to the molar charge concentration of the surfactant divided by the molar charge concentration of the ionically charged polymer, is between 0.01 and 100.

13. The particles as claimed in claim 12, wherein the ratio Zs is between 1 and 5.

14. The particles as claimed in claim 1, wherein the block copolymer is present in an amount, with the further proviso it has the same charge as the ionic ally charged polymer, such that the ratio Zb, corresponding to the molar charge concentration of the surfactant divided by the molar charge concentration of the ionically charged polymer and of the block copolymer, is between 0.5 and 1.5.

15. The particles as claimed in claim 1, wherein the block copolymer is present in an amount, with the further proviso it has a charge opposite to that of the ionically charged polymer, is such that the ratio Z'b, corresponding to the molar charge concentration of the surfactant and of the block copolymer divided by the molar charge concentration of the ionically charged polymer, is between 0.5 and 1.5.

16. The particles as claimed in claim 1, wherein the active substance is selected from compounds with low or no miscibility with water which are in solid or liquid form or in dissolved form in a water-immiscible solvent.

17. The particles as claimed in claim 1, wherein the active substance is present in an amount of between 0.01 and 100% by weight relative to the weight of ionically charged polymer, surfactant and block copolymer.

18. The particles as claimed in claim 1, wherein the particles are present in a concentration of between 0.1 and 50% by weight relative the aqueous phase.

19. A surface state modifier comprising particles as defined in claim 1.

20. A active substance carrier comprising particles as defined in claim 1.

21. A formulation for treating the skin or hair comprising particles as defined in claim 1.

22. A formulation for treating or forming metals comprising particles as defined in claim 1.

23. Particles comprising at least one ionically charged polymer, at least one surfactant having an ionic charge opposite to that of said polymer, at least one block copolymer consisting of one nonionic hydrophilic block A and one ionic block B, the particles optionally comprising at least one active substance, the internal structure of the particles forming a mesophase which is the organized phases of charged polymer/oppositely charged surfactant complexes, and the particles being in suspension in an aqueous phase, wherein the monomers from which the ionic block B are formed, are anionic monomers containing at least one carboxylic, sulfonic, sulfuric, phosphonic, phosphoric or sulfosuccinic function.

* * * * *